(12) United States Patent
Withers et al.

(10) Patent No.: US 8,431,541 B2
(45) Date of Patent: Apr. 30, 2013

(54) ALPHA-AMYLASE INHIBITORS: THE MONTBRETINS AND USES THEREOF

(75) Inventors: Stephen Withers, Vancouver (CA); Andrew C. Tarling, Vancouver (CA); Raymond Andersen, Vancouver (CA); Gary D. Brayer, Richmond (CA); Katherine Woods, Vancouver (CA)

(73) Assignee: The University of British Columbia (CA)

( * ) Notice: Subject to any disclaimer, the term of this patent is extended or adjusted under 35 U.S.C. 154(b) by 291 days.

(21) Appl. No.: 12/738,273

(22) PCT Filed: Oct. 16, 2008

(86) PCT No.: PCT/CA2008/001901
§ 371 (c)(1),
(2), (4) Date: Aug. 6, 2010

(87) PCT Pub. No.: WO2009/049428
PCT Pub. Date: Apr. 23, 2009

(65) Prior Publication Data
US 2011/0189107 A1    Aug. 4, 2011

Related U.S. Application Data

(60) Provisional application No. 60/960,843, filed on Oct. 16, 2007.

(51) Int. Cl.
*A01N 43/04* (2006.01)
*A61K 31/70* (2006.01)
*C07H 15/24* (2006.01)

(52) U.S. Cl.
USPC .......................................... 514/27; 536/18.1

(58) Field of Classification Search .................. None
See application file for complete search history.

(56) References Cited

FOREIGN PATENT DOCUMENTS

| EP | 0956867 A1 | 11/1999 |
|----|------------|---------|
| JP | 2002-010753 A | 1/2002 |
| JP | 2005-306836 A | 11/2005 |
| JP | 2007-070263 A | 3/2007 |
| WO | WO-2004/014159 A1 | 2/2004 |

OTHER PUBLICATIONS

Asada et al., Phytochemistry, 1988, 27(5), pp. 1497-1501.*
Nagamoto et al., Planta Med., 1988, 54(4), pp. 305-307.*
Asada et al. (1988). "Acylated flavonols from *Crocosmia crocosmiilora*," *Phytochemistry* 27(5):1497-1501.
Kawaguchi et al. (2007). "Isolation and characterization of a novel flavonoid possessing a 4,2"-glycosidic linkage from green mature acerola (*Malpighia emarginata* DC.) Fruit," *Biosci. Biotechnol. Biochem.* 71(5):1130-1135.
Lo Piparo et al. (2008). "Flavonoids for Controlling Starch Digestion: Structural Requirements for Inhibiting Human α-Amylase," *J. Med. Chem.* 51(12):3555-3561.
Nagamoto et al. (1988). "Antitumor constituents from bulbs of *Crocosmia crocosmiiflora*," *Planta Med.* 54(4):305-307.
Tadera et al. (2006). "Inhibition of α-glucosidase and α-amylase by flavonoids," *J. Nutr. Sci. Vitaminol* 52:149-153.
Tarling et al. (2008). "The search for novel human pancreatic α-amylase inhibitors: high-through put screening of terrestrial and marine nature product extracts," *ChemBioChem* 9:433-438.
Tundis et al. (2007). "Inhibitory effects on the digestive enzyme alpha-amylase of three *Salsola* species (Chenopodiaceae) in vitro," *Pharmazie* 62(6)473-475.
International Search Report mailed Feb. 9, 2009, for PCT Application No. PCT/CA2008/001901, 5 pages.
International Preliminary Report on Patentability mailed Apr. 20, 2010, for PCT Application No. PCT/CA2008/001901, 7 pages.
Agnihotri, V. et al. (2008). "Antioxidant constituents of *Nymphaea caerulea* flowers," *Phytochem* 69:2061-2066.
Kowalska, I. et al. (2007). "Flavonoids from Barrel Medic (*Medicago truncatula*) aerial parts," *J. Agric. Food Chem.* 55:2645-2652.
Lin, L-Z et al. (2008). "Chromatographic profiles and identification of new phenolic components of *Ginkgo biloba* leaves and selected products," *J. Agric. Food Chem.* 56:6671-6679.
Torres-Mendoza, D. et al. (2006). "Weakly antimalarial flavonol arabinofuranosides from *Calycolpus warszewiczianus*," *J. Nat. Prod.* 69:826-828.

* cited by examiner

*Primary Examiner* — Traviss C McIntosh, III
(74) *Attorney, Agent, or Firm* — Morrison & Foerster LLP

(57) ABSTRACT

Particular naturally occurring glycosylated acyl-flavonols are now shown to be effective mammalian α-amylase inhibitors. Such compounds can be obtained from plants of the genus *Crocosmia* and the compounds are useful in controlling starch digestion such as for management of glycemia in pre-diabetic or diabetic subjects, for management of obesity or for inhibiting oral caries or plaque formation.

25 Claims, 4 Drawing Sheets

ALPHA-AMYLASE INHIBITORS: THE MONTBRETINS AND USES THEREOF

RELATED APPLICATIONS

This application is a U.S. National Phase of International Application No. PCT/CA2008/001901, filed Oct. 16, 2008, which claims priority to U.S. provisional patent application 60/960,843 filed Oct. 16, 2007, the content of which is hereby incorporated by reference.

FIELD OF THE INVENTION

This invention relates to inhibitors of mammalian α-amylases.

BACKGROUND

Pancreatic α-amylase is an enzyme in the digestive system, catalyzing the initial step in the hydrolysis of starch, a principal source of glucose in the diet. It has been demonstrated that the activity of human pancreatic α-amylase (HPA) in the small intestine correlates to post-prandial glucose levels, the control of which is an important factor in diabetes and obesity. Salivary α-amylase is also involved in starch digestion and in the maintenance of the bacteria involved in oral plaque formation. Thus, modulation of α-amylase activity through the therapeutic use of inhibitors is of considerable medical relevance. Although two α-glucosidase inhibitors, acarbose (Precose™) and miglitol (Glyset™) have been used medically, their effectiveness may be limited by undesired side effects which may be due to non-specific inhibition of other α-glycosidases. These side effects may also be compounded by systemic absorption of these drugs and hence their distribution throughout the body. Unusually for an oral drug, poor absorption is a desirable quality for a pancreatic α-amylase inhibitor since the effect is only required locally (e.g. in the gut or oral cavity) and low systemic availability would reduce unwanted side effects.

Subsequent to filing of the related patent application noted above, it was reported that various flavonoids including myricetin inhibit human salivary α-amylase with $IC_{50}$ values in excess of about 9 or 10 µM (Lo Piparo, E. et al. "Flavonoids for Controlling Starch Digestion Structural Requirements for Inhibiting Human α-Amylase"; J. Med. Chem.; published on web May 29, 2008). As reported in the latter document, acarbose inhibited human salivary α-amylase with an $IC_{50}$ of approximately 1 µM. Previously, myricetin was reported as inhibiting porcine pancreatic α-amylase at an $IC_{50}$ value of 0.38 mM (Taderal, K. et al. (2006) J. Nutr. Sc., Vitaminol 52:149-153).

Asada, Y. et al. (1988) *Phytochemistry* 27, 1497-1501 described naturally occurring glycosylated compounds containing a myricetin moiety having the following structures.

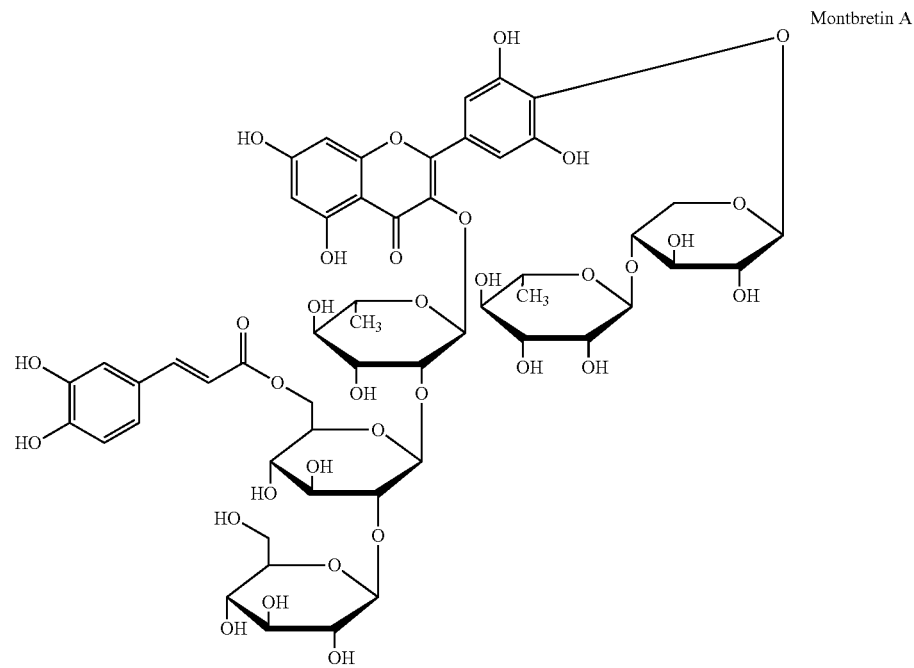

Montbretin A

-continued

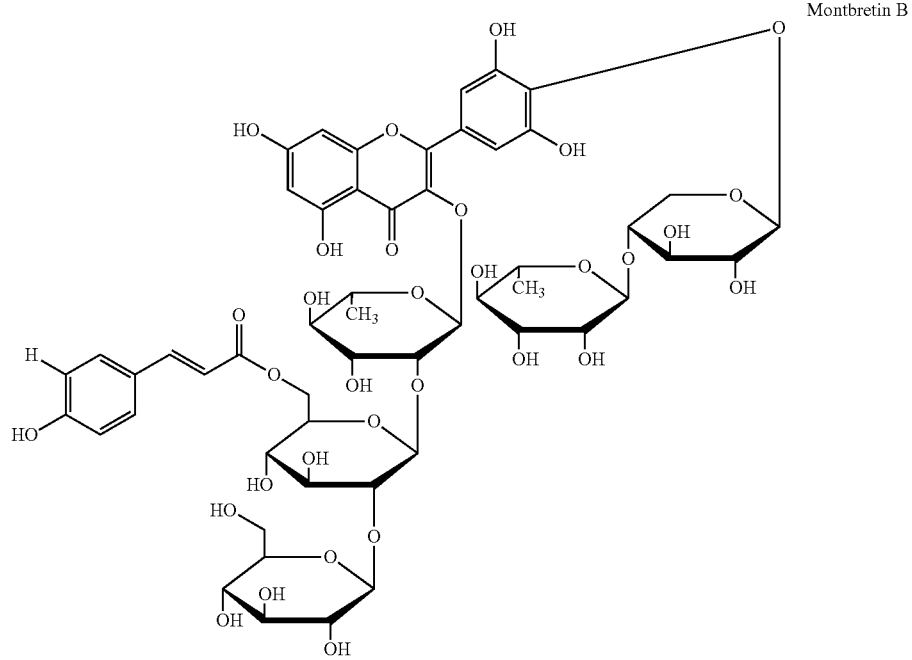

Montbretin B

Montbretin A and B were isolated from a common garden plant known as "Montbretia" which has been used as an anti-tumor remedy in Japanese folk medicine. However, no biological activity for montbretin A or B was reported.

SUMMARY OF THE INVENTION

This invention includes the use of certain glycosylated acyl-flavonols as mammalian pancreatic and salivary α-amylase inhibitors. Such compounds (or starting compounds for the preparation thereof) can be easily isolated in good yield from any species, hybrid or cultivar of *Crocosmia*, a genus of perennial plants of the Iridaceae family. The genus is native to South Africa, but is now found worldwide. The *Crocosmia* contains relatively few members and includes the hybrid generally known as "Montbretia". These compounds include montbretin A and B shown above and may be referred to herein collectively as "montbretin" or "montbretin compounds". The montbretin compounds are now shown to be useful in controlling starch digestion (for example to manage postprandial glycemia in pre-diabetic or diabetic subjects and/or for management of obesity in any subject) or for inhibiting oral caries and/or plaque formation. The subject may be a human or other mammal.

This invention also includes a novel compound having a methyl ester on the caffeic acid moiety and is named montbretin C as well as novel truncated derivatives of the naturally occurring montbretins in which the terminal glucose on the trisaccharide moiety is not present.

Montbretin A is the most potent α-amylase inhibitor of the montbretins, in addition to being the most abundant of the naturally occurring forms. Detailed kinetic analysis of montbretin A demonstrates it to be a tight binding competitive inhibitor of HPA with a high level of selectivity when tested against a series of other glycosidases.

DETAILED DESCRIPTION OF THE INVENTION

Figure 1:
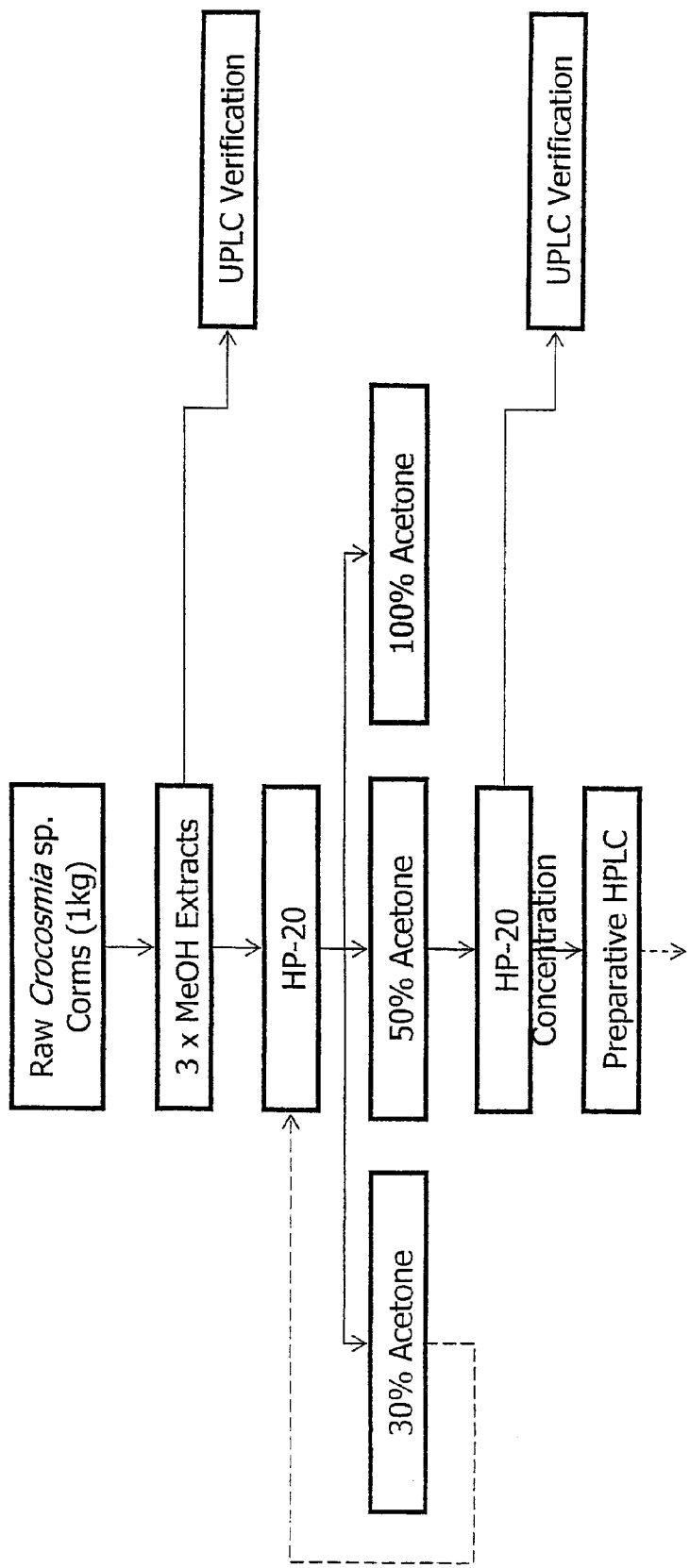
FIG. 1. A flow-chart showing a protocol for isolation of montbretins from the natural source using methanol (MeOH) extracts, HP-20 adsorbtion chromatography with an acetone: water mobile phase, preparative high pressure chromatograph (HPLC) and monitoring with ultra performance liquid chromatograph (UPLC).

Any terms not directly defined herein shall be understood to have the meanings commonly associated with them as understood within the art of the invention. Certain terms are discussed below, or elsewhere in the specification, to provide additional guidance to the practitioner in describing the compositions, devices, methods and the like of embodiments of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments of the invention herein.

This invention provides the use of a compound of formula I or a pharmaceutically acceptable salt thereof, as an α-amylase inhibitor in the treatment of pre-diabetes, diabetes, or obesity or for the prevention or treatment of dental caries or oral plaque or in the preparation of a composition for such use.

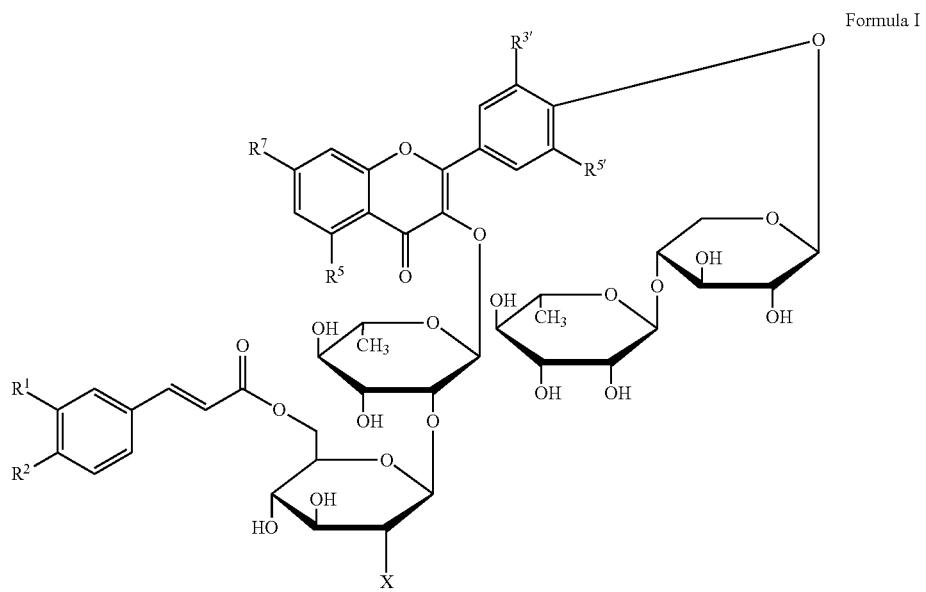

Formula I

In formula I, X is H, OH or a glucopyranosyl moiety. $R^1$, $R^2$, $R^5$, $R^7$, $R^{3'}$ and $R^{5'}$ are independently selected from H, OH and OR with R being an unsubstituted alkyl of 1-6 carbons in length, including methyl. In some embodiments, $R^1$ and $R^2$ may be replaced such that the carbon atoms to which they are attached are joined by a bridge having the structure (—O—$CH_2$—O—).

As used herein an 'alkyl' is a univalent, or free radical containing only carbon and hydrogen atoms arranged in a chain. The chain may be branched or unbranched. Unsubstituted, unbranched alkyls have a general formula $C_nH_{2n+1}$.

In some of the embodiments involving compounds of formula I, $R^7$ is OH and/or $R^{3'}$ is OH. In some of these embodiments, each of $R^{3'}$, $R^{5'}$, $R^5$ and $R^7$ is OH.

This invention also provides the use of a compound of formula II or a pharmaceutically acceptable salt thereof, as an α-amylase inhibitor in the treatment of pre-diabetes, diabetes, or obesity or for the prevention or treatment of dental caries or oral plaque, or in the preparation of a composition for such use. In formula II, $R^1$ and $R^2$ and X are as described above for formula I and $R^{3'}$, $R^5$, $R^{5'}$ and $R^7$ are —OH.

In particular embodiments involving compounds of formula I or II, $R^1$ is OH or —$OCH_3$ and/or $R^2$ is OH. In some of these embodiments $R^1$ is OH and $R^2$ is OH. In any or all of the aforementioned embodiments, X is —OH or a D-glucopyranosyl moiety. In particular embodiments, X has the following structure.

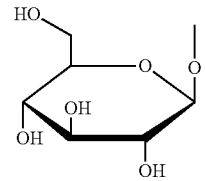

In another aspect of the invention there is provided a novel compound or a salt thereof of formula III. This compound may be made by transforming a naturally occurring montbretin, for example by reacting it with Br—$CH_2$—Cl and $C_5CO_3$ in DMF at elevated temperature.

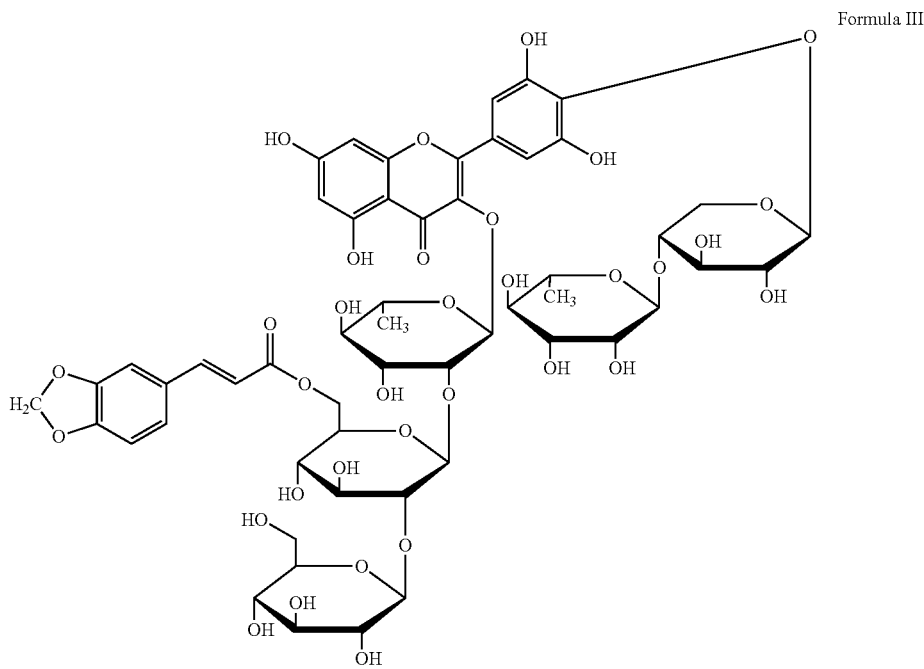

Formula III

In accordance with a further aspect of the invention there is provided compositions comprising one or more physiologically acceptable carriers and/or excipients, and at least one montbretin compound or a pharmaceutically acceptable salt thereof, for use in the treatment of pre-diabetes, diabetes or obesity, or for the treatment or prevention of dental caries or oral plaque.

In accordance with a further aspect of the invention there is provided novel, isolated montbretin compounds, or salts thereof or structural analogues thereof, excluding montbretin A and montbretin B.

The term "isolated" with regard to montbretins in this specification includes a condition whereby a naturally occurring montbretin compound is present in a preparation at any level of purity greater than that of the montbretin on a per weight basis in corm tissue of a *Crocosmia*, sp. For synthetic compounds (such as transformation products of a naturally occurring montbretin), the term "isolated" includes any preparation of that product, regardless of purity. Thus, the term "isolated" in this specification with regard to the montbretins, includes preparations enriched in a specified montbretin, as compared to natural sources. Examples include preparation having at least about 1.5 fold, 2.0 fold or at least about 2.5 fold increase in purity or more of the montbretin, as compared to the plant tissue. In order to determine a level of purification or enrichment, montbretins may be assayed for α-amylase inhibitory activity, for example using the procedures described herein.

Isolated, naturally occurring montbretins may be provided in the form of an extract from *Crocosmia*, sp. plant tissue, preferably an extract of the corm of such plants. *Crocosmia* corms typically comprise about 800 mg/kg (of montbretin A per kg of tissue). As is disclosed herein, montbretins (particularly montbretin A) are easily purified from corm tissue in good yield. The montbretins are typically water soluble and polar solvents may be advantageously employed for the preparation of such extract. Good results are obtained by extracting with water and short chain alcohols, including methanol and ethanol. Although isolated montbretins may be administered to an animal subject together with other compounds found in such a plant extract, minimization of side effects will occur through the use of substantially purified montbretin compounds, including a level of purity generally acceptable for pharmaceutical and/or food and beverage formulations.

Figure 2:
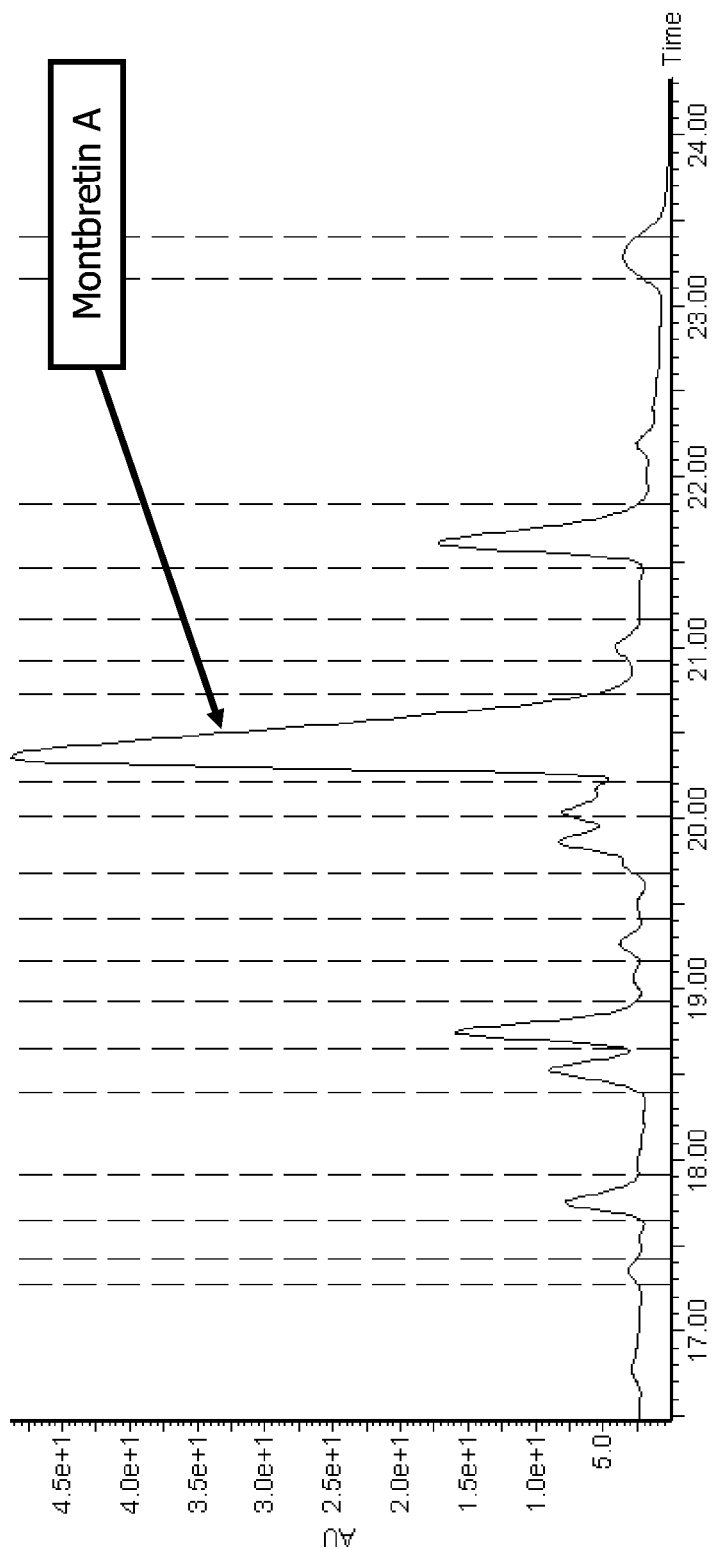
FIG. 2. A chart showing HPLC output with a Waters Autopurification System™ of an HP-20 purified sample as shown in FIG. 1, run on a gradient of 5% to 90% aqueous acetonitrile over 30 mM at 60 ml/min. The montbretin A fraction is labeled.

A variety of methods known in the art for obtaining flavonoids and the like from natural sources may be employed for isolation of montbretin compounds from plant tissue. Particular methodologies are disclosed in the Examples below. In addition, FIG. 1 outlines a simplified procedure useful for isolation of montbretins from corm tissue. Typically, the corms are sliced or minced and extracted overnight with methanol followed by vacuum filtration of the tissue. The extraction is typically performed twice more followed by rotary evaporation of the methanol in a 30° C. water bath. Long term storage of the resulting product is best done at −20° C. or less. The crude extract may then be subjected to adsorbtion chromatography on an appropriate column for scavenging of hydrophobic/organic materials. A good resin is that known as HP-20 such as that sold under the trademark Diaion. Rotary evaporated methanol extracts are dissolved in water and loaded onto the column which is eluted first with 30% acetone in distilled water followed by 50% acetone:water then 100% acetone:water. The majority of the montbretin compound will be found in the 50% acetone fraction. The eluent is typically evaporated to about 1% of its original volume and then subjected to preparative high-pressure liquid chromatography (HPLC) for example using the procedures as described in the Examples below. The isolation procedure may be monitored, for example by the use of ultra performance liquid chromatography (UPLC) and/or assays for α-amylase inhibitory activity. FIG. 2 shows the output of an HPLC preparation with the montbretin A peak identified.

Naturally occurring montbretins may also be subjected to a variety of transformations employing procedures known in the art. For example, sugars may be removed enzymatically or by hydrolysis and an example is the removal of the terminal glucose of the trisaccharide moiety in montbretin A-C using an enzyme such as is described in the examples herein. Removal of that glucosyl moiety does not affect α-amylase activity. Another example is the preparation of a compound of formula III as discussed above. Further examples of transformations include acylation of hydroxyl groups such as on the myricetin moiety of montbretin A-C. The following chart illustrates examples of routine chemical transformations that may be performed.

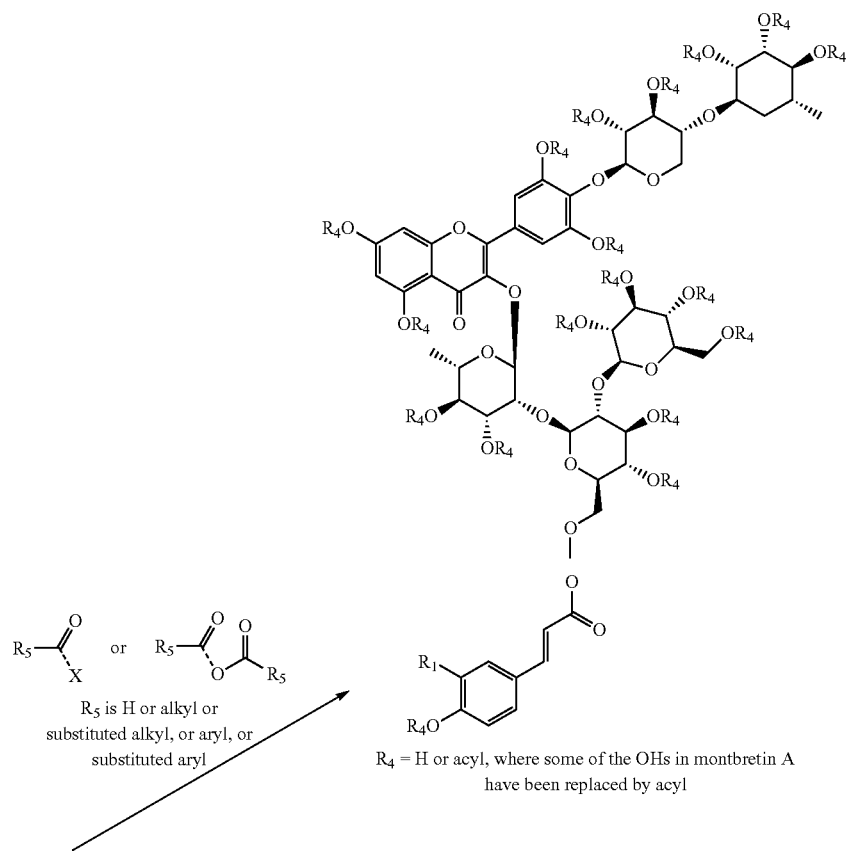

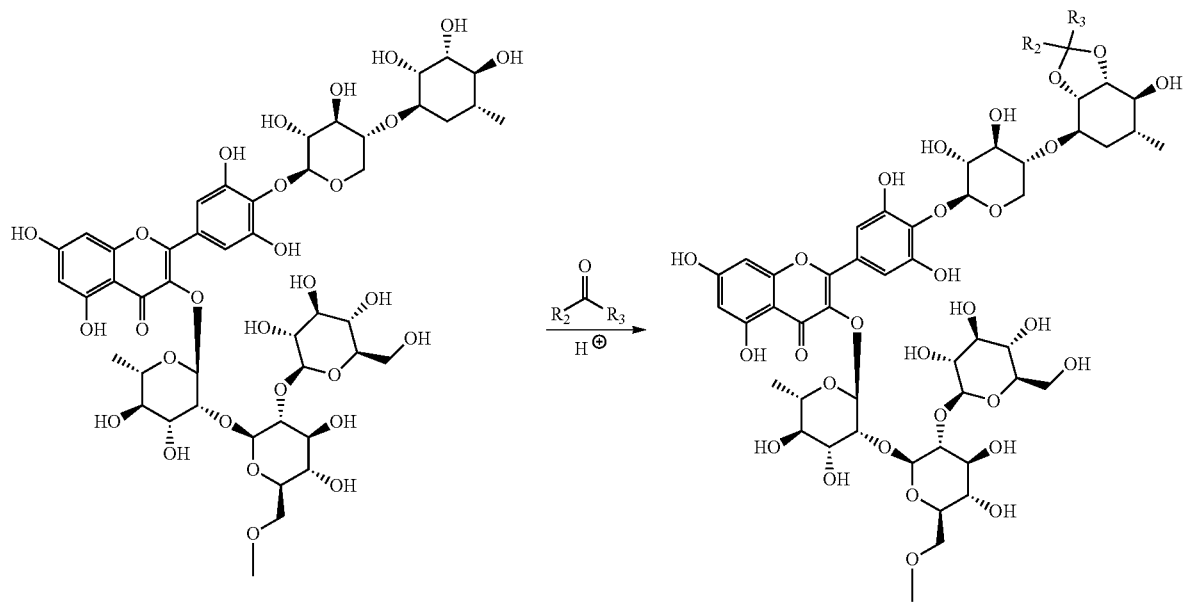

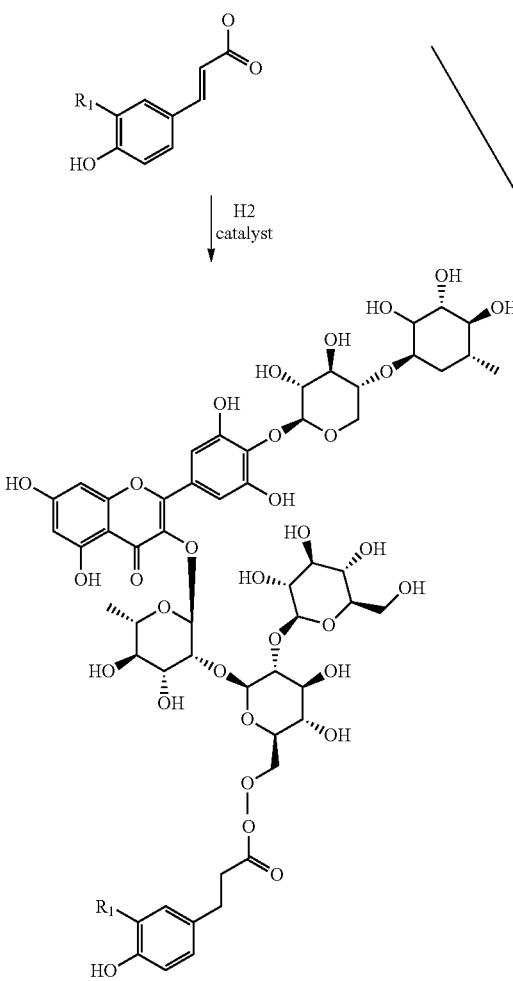

various ethers where OR₄ has replaced some
OF OH, i.e. R4 = H or alkyl

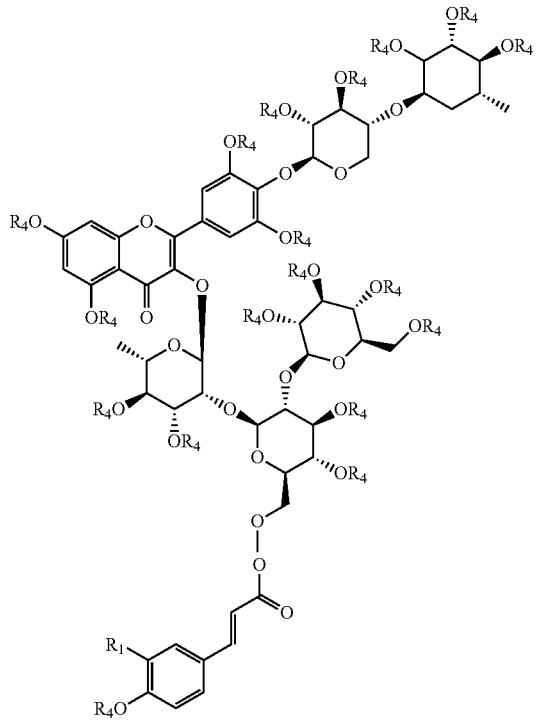

various ethers where OR₄ has replaced some
OF OH, i.e. R4 = H or alkyl

Compositions of this invention are generally administered orally to a subject and may be formulated by any means known in the art for oral uses. Compositions suitable for oral administration, including enteric administration may be provided in various forms including liquid, solids such as tablets or powders, pills or capsules, suspensions or gels, etc. Such compositions may be formulated for timed or sustained release. Various techniques are known to those of skill in the art of formulating oral pharmaceutical compositions, and may be found in, for example, Remington: the Science & Practice of Pharmacy by Alfonso Gennaro, 20th ed., Williams & Wilkins, (2000).

Compounds and compositions for use in this invention may also be administered by including an α-amylase inhibiting effective amount in a food, beverage, candy or other "treat", nutritional supplement, or the like, which is intended to be ingested by a subject. Compounds or compositions for use in this invention can be added to drinking water particularly for administration to animals.

For treatment or prophylaxis of dental plaque, caries, etc., compounds or compositions for use in this invention may be included in an effective amount to inhibit salivary α-amylase in the oral cavity in chewing gum, mouthwash or other oral rinses, toothpaste or any other composition intended to be applied to the oral cavity or teeth.

In some embodiments of this invention the natural montbretins may be prepared and administered according to various means known in the art for plant products. A non-exhaustive list of examples are plant extracts and formulations, teas, tinctures, vinegar tinctures, syrups and oral topical preparations including salves. Various techniques are known to those of skill in the art of medicinal plant extracts, and may be found in, for example, How to be Your Own Herbal Pharmacist by Linda Page, 2$^{nd}$ ed. Healthy Healing Publications (1997).

As is disclosed herein, effective amounts of the montbretins may be used to treat a subject in need thereof for any condition benefited by the inhibition of salivary or pancreatic α-amylase. Examples include the treatment of pre-diabetes, diabetes and/or obesity through the inhibition of pancreatic α-amylase. Another example is the prophylaxis or treatment of dental caries and/or plaque as a result of the inhibition of salivary α-amylase. It is well within the skill of the medical practitioner to determine an "effective amount" depending upon the nature of the animal subject and whether the target enzyme is salivary or pancreatic. Based on the animal trials disclosed in the Examples herein, examples of doses of montbretin A that may be employed to manage blood glucose levels in diabetics may be in the range of about 0.5 mg/kg to about 60 mg/kg per day. Montbretins may be administered in association with each meal or about 3 times a day or they may be formulated for continuous administration.

Natural sources for the montbretins include any member of the genus *Crocosmia*, including all species, hybrids and cultivars thereof. Plants of this genus are now common throughout the world as garden plants. These plants produce abundant corm tissue and the corms may also be purchased commercially since they are used in addition to seed for reproduction of the plants. A text describing plants of the genus *Crocosmia* is Goldblat, P. et al. "*Crocosmia and Chasmanthe*" Royal Horticultural Society; Timber Press; Oregon USA.

Examples of members of the *Crocosmia* genus are *Crocosmia crocosmiiflora, Crocosmia ambongensis, Crocosmia aurea* (Falling Stars), *Crocosmia cinnabarina, Crocosmia fucata* (Namaqualand, Cape region), *Crocosmia luciferans, Crocosmia maculata, Crocosmia masonorum* (Giant Montbretia), *Crocosmia mathewsiana, Crocosmia paniculata* (Aunt-Eliza), *Crocosmia pauciflora, Crocosmia pearsei, Crocosmia pottsii, Crocosmia x crocosmoides, Crocosmia x latifolia*, and the cultivars: 'His Majesty' (flowers large, orange), 'Jackanapes' (flowers orange-red, inner lobes golden yellow), and 'Solfatare' (yellow flowers with bronze foliage).

Other aspects and features of the present invention will become apparent to those ordinarily skilled in the art upon review of the following description of specific embodiments of the invention in conjunction with the accompanying figures. The invention is herein further described with reference to the following, non-limiting, examples. A description of the experimental procedures employed follows the examples.

EXAMPLE 1

HPA Inhibition Screening

The assay for HPA activity was based upon the enzymatic cleavage of a synthetic aryl glycoside substrate to yield a chromophoric product, the release of which can be monitored in a continuous fashion. The commercially available amylase substrate 2-chloro-4-nitrophenyl α-D-maltotrioside (CNP-G3) is used since the pKa of the chloronitrophenyl leaving group (pKa 6.4) is considerably lower than the pH value of the assay (pH 7.0), hence a high extinction coefficient for the chromophore is obtained. The assay solution also included Triton X-100™ (0.01%) to minimize the detection of promiscuous inhibitors. The samples in the initial screen were DMSO solutions containing 5 mg/mL of dried methanolic extracts, tested at a dilution of 60 nL in a final assay volume of 60 μL (5 μg/mL final extract concentration). The enzymatic activity of HPA was found to be completely unaffected by the addition of this small amount of DMSO (0.1%) and Triton X-100™ (0.01%). Each sample was run in duplicate with the replicate run on a separate plate. Two test plates containing a serial dilution of the known HPA inhibitor acarbose were run as the first and last plate of each batch in order to ensure the robustness and integrity of the assay for each given batch analyzed.

The screen was performed on a Beckman Coulter Biomek FX Laboratory Automation Workstation equipped with a 96 channel pipetting head and a low volume 96 pin High Density Replicator™. This workstation is integrated with a Beckman Coulter DTX880™ plate reader with UV/Vis capability allowing for sequential assay plate processing and reading. The assay was run in 384 well plates containing a 60 μL volume of 50 mM sodium phosphate buffer (pH 7.0), 100 mM sodium chloride, CNP-G3 (1 mM final concentration), HPA (1 μg/mL final concentration) and Triton X-100™ (0.01%). The CNP-G3 substrate was employed at a sub $K_M$ concentration ($K_M$=3.6 mM). The extracts were added to the assay plate using three transfers of the High-Density Replicator™ pin tool (20 nL volume per transfer). Each sample was run in duplicate with the second duplicate run on a separate plate additionally containing 4'-O-methyl-maltosyl-α-D-fluoride (1 mM final concentration). All of the assay plates contained 32 high controls (no inhibitor). The inhibitors and enzyme were allowed to incubate together at room temperature for 10 minutes to allow for detection of "slow-on" type inhibitors. The reaction was initiated by addition of substrate and the subsequent release of the chloronitrophenolate anion was monitored continuously at 405 nm for 7 minutes. The plate reader software (Beckman Coulter Multimode Detection™) was then used to calculate the rate of the reaction in each well. The rate for each extract was normalized with respect to the high controls, and the data for each sample reported as % residual activity. For each sample the two replicates were plotted against one another (x, y), and those samples which fell within the hit window (set at 3 standard deviations from the mean of the sample set) were selected for validation. An aliquot (1 μL) of each of the extracts was retested in a half-area 6 well plate (100 μL final volume), and those samples that gave reproducible inhibitory activity were identified as "true hits".

30,000 extracts from the National Cancer Institute U.S.A. (NCI), were screened using the above described procedures. The data for each plate were normalized relative to the high controls to evaluate data quality. The average Z' statistic, which represents the quality of the control samples and provides an indication of assay suitability, was determined to be 0.86. Additionally, the average Z value of 0.82, which represents how well the library is tolerated, demonstrated that the assay was remarkably robust and the data therein very reliable. The hit threshold was set at 3 standard deviations from the mean of the sample set (corresponding to 81% residual activity) and samples for which both replicates fell within the hit boundary were selected for further investigation.

The majority of the samples exhibited around 100% residual activity for both replicates as would be expected for a sample set where the extracts are predominantly non-inhibitory. Only samples in which both replicates fell within the hit boundary were selected for further validation. 30 extracts identified as hits from the primary screen, each hit was re-evaluated manually on a standard UV/Vis spectrophotometer. In the secondary screen, 25 of the extracts gave reproducible inhibition, confirming them to be "true hits"; whereas 5 extracts showed no significant HPA inhibition, thus identifying themselves as false positives.

EXAMPLE 2

Bio-Assay Guided Isolation of HPA Inhibitors

The extract from Example 1 with the most significant inhibitory activity (2% residual activity) was selected for further study. Prior to detailed investigation of the active components, a preliminary kinetic analysis of the HPA inhibition was performed on the crude extract. A dilution series showed a semilogarithmic sigmoidal dose-response curve typical of a "well-behaved" inhibitor, and revealed a very low $IC_{50}$ value of 0.54±0.01 µL/100 µL (extract volume/assay volume). Additionally, the crude extract showed no time-dependent inactivation of HPA, with the level of inhibition remaining constant for over 4 hours. These tests indicate an absence of undesirable modes of action such as enzyme denaturation or covalent enzyme modification. This extract was a dried methanolic extract of the bulbs from Crocosmia sp.

In order to isolate the principal bioactive components from the complex mixture of the extract, a series of bioassay-guided purification steps as described below were performed on a larger quantity of the crude material obtained from the NCI open plant repository. At each step, the column fractions were assayed for HPA inhibition using the assay described above, and the active fractions taken forward.

The crude material (2 g) was partitioned between ethyl acetate and water, with the aqueous fraction then partitioned against butanol. The butanolic fraction was applied, 150 mg at a time, to a column packed with Sephadex™ LH-20 pre-swollen in methanol for size exclusion chromatography. The resulting fractions were grouped based on biological activity. The active fraction was purified by HPLC using 22% aqueous acetonitrile, to afford three fractions. Further purification of the main fraction using a gradient from 30% to 40% aqueous acetonitrile over 30 minutes afforded montbretin A (15 min, 8.4 mg) as a yellow powder. A gradient from 30% to 70% aqueous acetonitrile over 30 minutes on the second fraction afforded montbretin B as a yellow powder (16 min, 0.9 mg), and a gradient from 20% to 30% aqueous acetonitrile was used on the third fraction, which afforded montbretin C (20 min, 1.6 mg) as a yellow powder.

Column fractions from each step of the purification process were sub-sampled (100 µL) into 96 well plates which were then allowed to evaporate to dryness. Using the Biomek FX™ the fractions were redissolved in water and varying aliquots (1-10 µL) were transferred to a 384 well plate where they were analyzed for HPA inhibitory activity using the protocol described in Example 1.

Optical rotations were determined using a JASCO J-1010™ polarimeter equipped with a halogen lamp (589 nm) and a 10 mm micro cell. UV spectra were recorded on a Waters 2487™ spectrophotometer. $^1H$, $^{13}C$, COSY, HSQC, HMBC, TOCSY and ROESY spectra were recorded on a Bruker AV600™ NMR spectrophotometer equipped with a cryoprobe. Chemical shifts were referenced to solvent peaks ($\delta H$ 3.31, $\delta C$, 49.15 for $CD_3OD$). ESI mass spectra were recorded using a Micromass LCT™ mass spectrometer. HPLC separations were performed using a Waters 600™ pump and a Waters PDA900™ detector, using an Inertsil C18™ column, 9.4×250 mm, flow 1 mL/min. All solvents were HPLC grade (Fisher) and filtered prior to use, then sparged with helium.

After purification, a family of three related compounds was obtained. Through a combination of 2D-NMR spectroscopy and mass spectrometry two of these compounds were identified as montbretin A and B. The remaining family member was identified as a methyl ether of the cinnamic acid moiety and named montbretin C (Table 1).

TABLE 1

| Montbretin | $R_1$ |
|---|---|
| A | OH |
| B | H |
| C | OMe |

Montbretin A was identified using a combination of MS data, 1 and 2D NMR techniques and a comparison to earlier literature data (Asada, et al. [supra]). Standard techniques (COSY, HMBC and ROESY) were used to link together the sugars and the aromatic portions. The aromatic portions of montbretin A were completely elucidated using HMBC and COSY data. The identity of the sugar residues was obtained and confirmed using 1D-TOCSY and ROESY data, and was found to be in agreement with the assignments in the literature. Montbretin B was also identified via 1 and 2D NMR techniques, as well as comparison to the spectra of montbretin A and to the literature data.

The structure of montbretin C was assigned based on MS, 1 and 2D NMR data, and by comparison with the spectra of montbretin A. The spectra of montbretin C appeared identical, except for an additional strong singlet at 3.71 ppm in the $^1H$ spectrum, and a new carbon at 55.8 ppm in the $^{13}C$ spectrum. Additionally, montbretin C is 14 mass units higher than montbretin A, leading to the conclusion that montbretin C is a methyl ether of montbretin A. Examination of the 2D HMBC and 2D ROESY data led to the conclusion that the methyl ether is on C6.

These naturally occurring montbretins, which contain a myricetin flavonol core, are glycosylated at the 3 and 4' positions. The 3 hydroxyl carries an α-linked linear trisaccharide consisting of D-glucopyranosyl-(β1→2)-D-glucopyranosyl-(β1→2)-L-rhamnopyranose, with the central D-glucosyl sugar bearing a 6-O-cinnamic ester which is differentially substituted among the family members. The 4' position bears a β-linked D-xylose unit, itself appended on its 4-hydroxyl with an α-linked L-rhamnopyranosyl moiety.

EXAMPLE 3

Kinetic Analysis

The $K_i$ values and mode of inhibition of montbretin A, myricetin and ethyl caffeiate were determined by measuring the rate of reaction at differing inhibitor concentrations for a series of substrate concentrations. Reactions were performed on either a Varian Cary300™ or Cary4000™ UV/Vis spectrophotometer at 400 nm. The substrate concentration (CNP-G3) was typically varied from ⅕ to 5 times the $K_M$ value. A similar range of inhibitor concentrations was attempted but some limitations were encountered. The lowest concentration of montbretin A that could be measured was 4 nM (½ the $K_i$ value) due to the very low enzyme concentration required to remain significantly below the inhibitor concentration. Conversely the limited aqueous solubility of myricetin and ethyl caffeiate meant that the highest inhibitor concentration determined for these compounds was 1.5 times the $K_i$ value. Double reciprocal plots of the data for montbretin A and myricetin indicated both compounds to be competitive inhibitors of HPA. $K_i$ values of 8.1±0.5 nM and 110±15 μM respectively were determined in using the analysis program GraFit™. A double reciprocal plot of the data obtained with ethyl caffeiate demonstrated it to be a non-competitive inhibitor of HPA with a $K_i$ value of 1.3±0.1 mM as determined using the GraFit™ program.

$K_i$ values of montbretins B and C were determined by the range finder method. The rate of reaction for a series of varying inhibitor concentrations was measured at a fixed substrate concentration. From a Dixon plot of the data the intercept of the line of best fit through these points with the $1/V_{max}$ line is equal to the $-K_i$ value. From these data $K_i$ values of 3.6±0.1 μM and 6.1±0.1 μM were obtained for montbretins B and C respectively.

Kinetic analyses of the three family members isolated showed montbretin A to be a considerably more potent inhibitor of HPA (Ki in the nanomolar range) than montbretins B and C (Ki in the micromolar range; see Table 2). The presence of the free meta-hydroxyl group of the cinnamic acid moiety appears important to tight binding of montbretin A since its removal or methylation (montbretins B and C respectively) lowers HPA inhibitory activity.

TABLE 2

Inhibition of HPA by Montbretins A-C

| Montbretin | $R_1$ | $K_i$ (nM) |
|---|---|---|
| A | OH | 8.1 |
| B | H | 3600 |
| C | OMe | 6100 |

Additionally, montbretin A showed a high level of selectivity towards HPA when tested against a series of glycosidases, including other GH13 enzymes (Table 3).

TABLE 3

Glycosidase Specificity of Montbretin A

| Glycosidase | RA (%)[a] |
|---|---|
| α-amylase (HPA) | 11% |
| β-glucosidase (*Agrobacterium* sp.) | 100% |
| β-galactosidase (*E. coli*) | 98% |
| β-hexosaminidase (Jack Bean) | 99% |
| α-mannosidase (Jack Bean) | 100% |
| α-galactosidase (Green Coffee Beans) | 100% |
| α-glucosidase (Brewers Yeast) | 97% |

[a]Residual Enzyme Activity at 0.1 μM Montbretin A

Given that flavonoids are known to possess both antioxidant and prooxidative properties, and initial concern was that montbretin A may inactivate HPA through redox modifications. In order to refute this possibility, inhibition of HPA by montbretin A was measured both in the presence and absence of 5 mM dithiothreitol (DTT). DTT would maintain the enzyme and reagents in a reducing environment, thereby preventing the occurrence of any redox chemistry either in solution or within the enzyme active site. No effect on HPA inhibition was observed upon the inclusion of DTT.

Additionally, flavonoids can also chelate metal cations raising the possibility that the inhibitor may be extracting the essential HPA calcium ion. In order to discount this mechanism of action, kinetic studies were performed in the presence of 1 mM calcium chloride and no change in inhibition was noted.

In order to investigate the structural motifs of the montbretins which contribute to α-amylase inhibition, commercially available compounds that correspond to the two aromatic portions; the flavonol core (myricetin) and the 6-O-acyl group (caffeic acid) were examined independently as HPA inhibitors. Myricetin was found to be an HPA inhibitor ($K_i$=110 μM), albeit several orders of magnitude reduced from montbretin. The inhibition was observed to be of a competitive nature, indicating that inhibition arises from binding in the enzyme active site. Ethyl caffeinate, the ethyl ester of caffeic acid, was found to be a weak inhibitor of HPA ($K_i$=1.3 mM). The inhibition mode in the latter case was observed to be non-competitive, suggesting that inhibition is arising through interactions remote from the active site. Without being bound to the following, these findings suggest a model in which the flavonol core occupies the active site while the caffeic acid moiety binds to a second site, with the sugar residues acting as linkers, and quite possibly also providing additional binding interactions.

Montbretin A demonstrated time dependent inhibition towards the β-glucosidase from *Agrobacterium*, (Abg), with the extent of inhibition decreasing with time. Pre-incubation of montbretin A with Abg prior to addition of the assay substrate resulted in no inhibition being observed. Abg is promiscuous with regards to the substrate aglycone, hence it seems that montbretin A acts as a substrate for Abg and the terminal β-linked glucose residue is cleaved. The subsequent residue of montbretin A is also a β-linked glucose residue, however this residue bears a large 6-O-caffeic ester moiety and would therefore not be processed by Abg. Upon re-testing of the truncated montbretin A-derived compound, no significant change in the inhibitory potency with respect to HPA was observed. Thus, the terminal glucosyl residue on the trisaccharide moiety is not required for α-amylase activity.

EXAMPLE 4

Gastric Stability of Montbretin A

The stability of montbretin A in both simulated intestinal fluid (SIF) and simulated gastric fluid (SGF) were analyzed via ultra performance liquid chromatography (UPLC). The instrument consisted of a Waters® Acquity™ UPLC system equipped with a PDA and a TQ detector in tandem. The 2 μL sample injection volume was passed through a Waters® Acquity™ BEH C18 column (1.7 μm, 2.1×100 mm), with mobile phases A and B consisting of water with 0.1% formic acid and acetonitrile with 0.1% formic acid, respectively. The mobile phases were delivered at a programmed linear gradient at a column temperature of 35° C. Linearity was evaluated using a set of montbretin A calibration standards with concentrations ranging from 10 to 100 μg/mL in water.

For the SGF stability studies, 2.0 g of sodium chloride and 3.2 g of pepsin from porcine stomach mucosa 1:2,500 was dissolved in 7.0 mL of hydrochloric acid and 200 mL of de-ionized water. The resulting solution was diluted to 1 L with de-ionized with a pH of 1.51. For the SIF, 26.8 g of monobasic potassium phosphate was dissolved in 250 mL of de-ionized water and mixed, followed by addition of 77 mL of 0.2 N sodium hydroxide and 500 ml of de-ionized water. 10 g of pancreatin, porcine pancreas was then added and mixed. The resulting solution was adjusted to a pH of 6.89 with 0.2 N sodium hydroxide and diluted to 1 L with de-ionized water.

To examine the gastrointestinal fluid activity, 0.5 mg/ml solutions of oleamide (positive control) in SGF or SIF were prepared by diluting a 100 μL aliquot of oleamide (50 mg/mL in 2-propanol) to 10 mL with either SGF or SIF and incubated in a 37° C. water bath for 1 or 3 hours, respectively. At time points of 1 or 3 hours, the sample was removed from the water bath and a 100 μL aliquot of the resulting solution was diluted to 1 mL with de-ionized water in a glass UPLC glass sample vial and analyzed by UPLC for oleamide content. Simulated gastric fluid activity was chromatographically analyzed upon the ability of the gastrointestinal fluids ability to degrade the oleamide to oleic acid. Oleamide in the presence of either SGF or SIF displayed a significant decrease in concentration after incubation when compared to at the measured gastric stability study time points.

Stability of montbretin was examined by preparing a 0.5 mg/ml solutions of montbretin A in either SGF or SIF by diluting appropriate aliquots of 5 mg/ml of montbretin A in water with SGF or SIF. For stability of montbretin A in SGF, five 1 mL aliquots of montbretin A in SGF were transferred into separate glass vials and placed in a 37° C. water bath. At time points of 0, 15, 30, 45 and 60 min, one vial was taken out of the water bath and 1 mL of methanol was added to the solution and vortexed. 200 μl of the resulting solution was transferred into a glass UPLC sample vial and diluted to 1 mL with de-ionized water and analyzed by UPLC for montbretin A content. For stability in SIF, four 1 mL aliquots of montbretin A solution is SIF in separate glass vials were placed in a 37° C. water bath for time points of 0, 1, 2 and 3 hr and similarly analyzed as described above.

The stability of montbretin A in SGF was examined at time points of 0, 15, 30, 45, and 60 minutes and in SIF, the stability was examined at time points of 0, 1, 2 and 3 hour. A slight decrease of montbretin A was observed in the simulated gastric environment whereas in the simulated intestinal environment, no significant decrease was observed. The level of degradation or loss of montbretin A in SGF was ~10% at 1 hour whereas in SIF, no significant degradation was observed within 3 hours of incubation at 37° C.

EXAMPLE 5

Plant Sources and Extracts Thereof

Corm tissue from a cross-section of all the major original *Crocosmia* species and their hybridizations were tested for the presence of montbretins. Those tests included: *Crocosmia x crocosmiiflora [Crocosmia pottsii x Crocosmia aurea]*; *Crocosmia x crocosmiiflora* 'Emily McKenzie' [*Crocosmia pottsii x Crocosmia aurea*]; *Crocosmia* 'Emberglow' [*Crocosmia pottsii x Crocosmia paniculata*]; *Crocosmia* 'Lucifer' [*Crocosmia masoniorum x Crocosmia paniculata*]. In each case, at least montbretin A and B were found with A being the predominant compound. In addition, various liquid extracts of the corm tissue were tested for the concentration of montbretins. The best results in terms of yield were obtained using water based slurries of corm tissue, aqueous extracts, methanolic extracts followed by ethanolic extracts.

EXAMPLE 6

Acute Starch Tolerance Test (Acarbose)

A study was done to determine the effect of acarbose on plasma glucose levels in response to a starch challenge in control and STZ-diabetic rats. Twenty-four animals were obtained at 200-250 g of body weight and randomly divided into control and diabetic groups. Diabetes was induced by a single intravenous tail vein injection of streptozotocin 60 mg/kg in 0.9% normal saline. Control rats received normal saline injections only. Animals were subsequently divided into acarbose untreated and treated. The four treatment groups were: control, n=6, control+acarbose, n=6, diabetic, n=6 and diabetic+acarbose, n=6. Starch was obtained from Fisher Scientific and a 17.5% suspension was made in distilled water. The dose of starch given was 2 kg/g. Acarbose was dissolved in distilled water at a concentration of 10 mg/ml and given at a volume of 1 ml/kg. The dose of acarbose given was 10 mg/kg.

Figure 3:
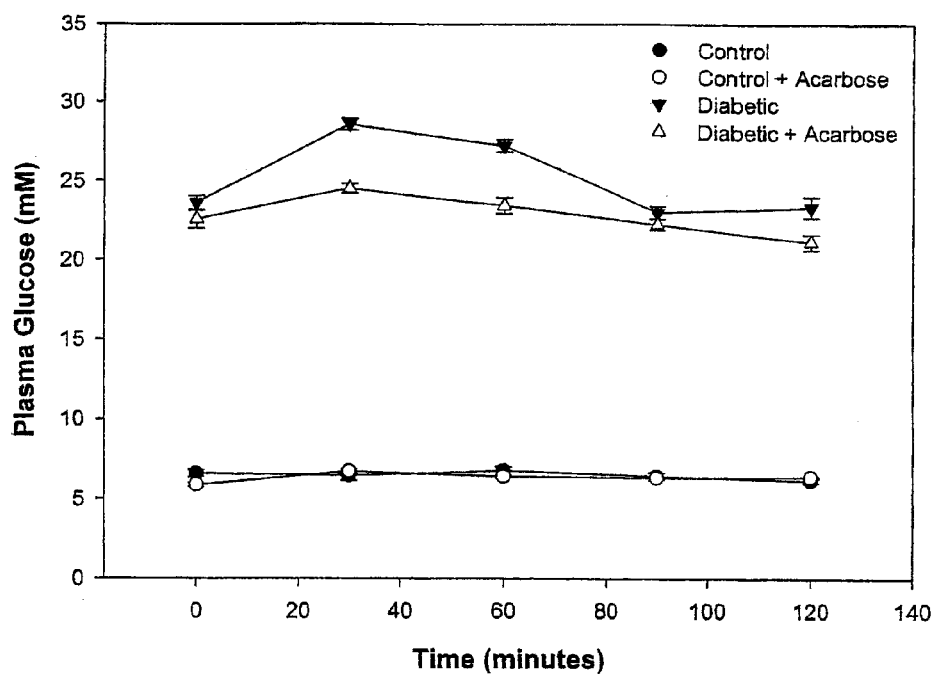
FIGS. 3 to 6 are graphs of starch tolerance tests using acarbose, montbretin A and alcoholic extracts of corms of *Crocosmia*, sp.

The animals were fasted overnight. A basal blood sample was collected (50 μl volume) and then at 30, 60, 90 and 120 minutes post drug administration. Starch and starch+acarbose was administered by oral gavage. Blood was centrifuged at 10,000 g×25 minutes and plasma collected for determination of glucose levels using a Beckman Glucose Analyzer II™. Results are shown in FIG. 3. There was no difference in body weight among the groups. There was a significant increase in plasma glucose 30 and 60 minutes following starch administration in the diabetic untreated group only. Thus, acute administration of acarbose on rats at a dose of 10 mg/kg is effective in preventing the increase in plasma glucose following a starch challenge

EXAMPLE 7

Acute Starch Tolerance Test (Montbretin A)

A second study was done to determine the effect of montbretin A on plasma glucose levels in response to a starch challenge in control and STZ-diabetic rats.

Figure 4:
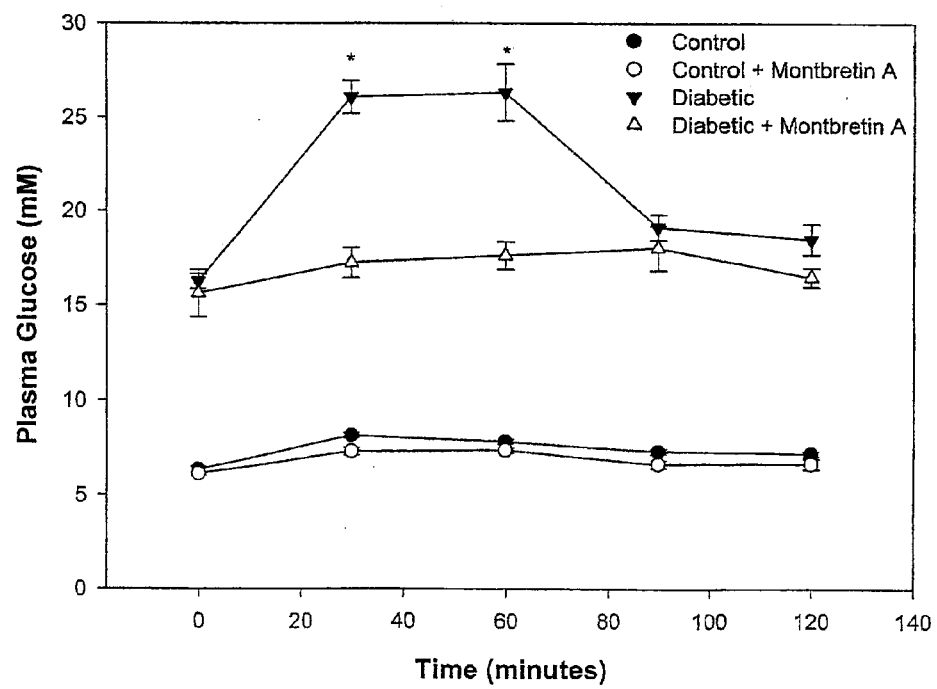

The twenty-four animals from Example 6 were used following a wash out period of one week. Animals were divided into montbretin A untreated and treated. The four treatment groups were: control, n=6, control+montbretin A, n=6, diabetic, n=6 and diabetic+montbretin A, n=6. The procedures used in Example 6 were employed. Montbretin A was dissolved in distilled water at a concentration of 10 mg/ml and given at a volume of 1 ml/kg. The dose of montbretin A given was 10 mg/kg. The results are shown in FIG. 4. There was no difference in body weight among the groups. There was a significant increase in plasma glucose levels in the diabetic untreated group at 30 and 60 minutes following starch administration. Thus, acute administration of montbretin A on rats at a dose of 10 mg/kg is effective in preventing the increase in plasma glucose following a starch challenge.

EXAMPLE 8

Acute Starch Tolerance Test (Plant Extracts and Montbretin A)

A study was done to determine the effect of various amounts of montbretin A and montbretin extracts on plasma glucose levels in response to a starch challenge in STZ-diabetic rats. Diabetic animals used in the previous Examples were used following a wash out period of one week. The six experimental groups were: diabetic (D, n=3) diabetic+montbretin A (5 mg/kg), (DT5, n=3), diabetic+montbretin A (1 mg/kg), (DT1, n=3), diabetic+montbretin A (0.5 mg/kg), (DT0.5, n=3), diabetic+*Crocosmia* corm methanol extract (5 mg/kg), (DM, n=3) and diabetic+*Crocosmia* corm ethanol extract (5 mg/kg), (DE, n=2).

Figure 5:
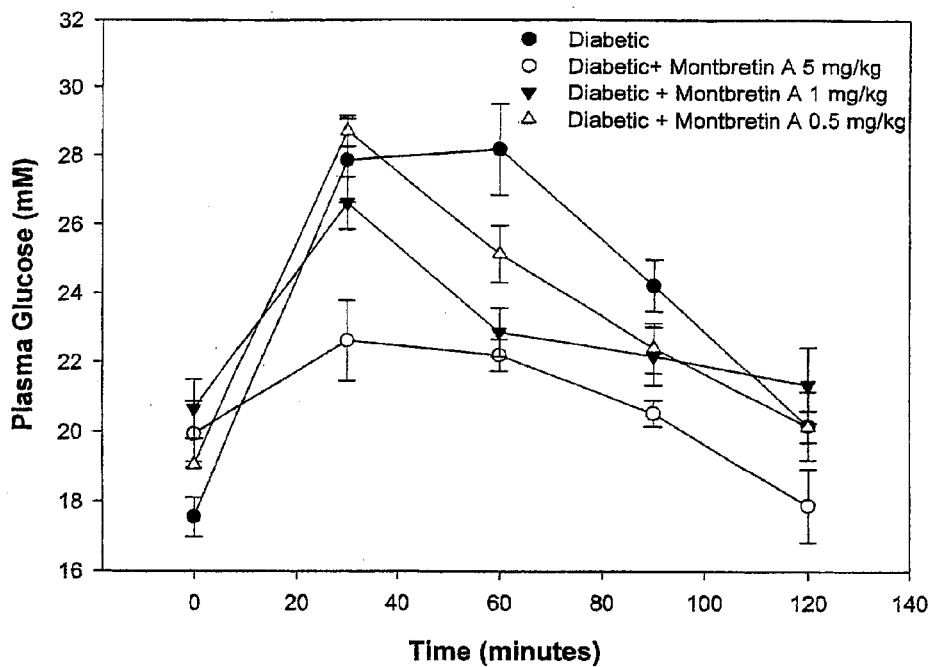
Figure 6:
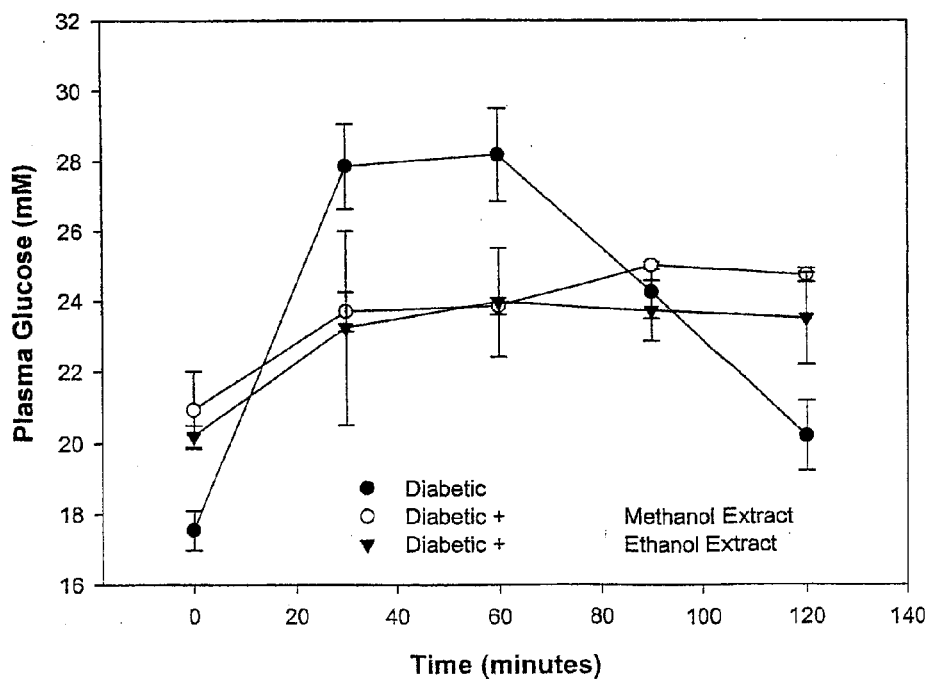

Montbretin A was dissolved in distilled water at a concentration of 5, 1 or 0.5 mg/ml and given at a volume of 1 ml/kg. The methanol extract contained montbretin A at a concentration of 3.2 mg/ml and ethanol extract at a concentration of 1.6 mg/ml. These extracts were dried and resuspended in distilled water. The procedure of Examples 6 and 7 were followed and the results are shown in FIGS. 5 and 6. There was no difference in body weight among the groups. Acute administration of montbretin A at 5 mg/kg prevented the increase in plasma glucose following starch administration. While there was an indication of an effect with the lower doses on rats, it was not particularly significant when area under the curve was determined. Diarrhea occurred in 2 out 3 animals given the methanol extract and in 1 out of 2 animals given the ethanol extract. Diarrhea was moderately severe at the 60 and 90 minute time points in animals in both the methanolic (1 of 3) and the ethanolic extract groups. Diarrhea appeared to have been resolved by the 120 minute time point. No diarrhea was noted on animals dosed with the purified montbretin.

EXAMPLE 9

Taste Aversion

A study was done to determine if there is aversion by animals to the taste of montbretin A dissolved in drinking water. Six (6) male Wistar rats weighing between 500-650 g were housed 2 rats per cage. Three hundred grams (300 g) of standard rat chow (Purnia) was placed in the food hopper of each cage daily. Food consumption per cage per day was determined every 24 hours for 3 days. A fluid volume of 900 ml of drinking water was placed on each cage daily. Fluid consumption per cage per day was determined every 24 hours for 3 days. Body weights of each animal were measured every 24 hours.

Based on the preliminary drinking water values obtained, montbretin A was dissolved in the drinking water so as to deliver a dose of 10 mg/kg/day. Body weight and food consumption measurements were done as described above. A fluid volume of 250 ml of montbretin A solution at a concentration of 0.09 mg/ml was placed on each cage daily. Fluid consumption was measured every 24 hours for 3 days.

The food and fluid consumption and body weights were analyzed. The dose of montbretin A was determined based on weight and consumption values. There was no effect of montbretin A dissolved in the drinking water on body weight, fluid intake or food intake and a dose of approximately 10 mg/kg was achieved. There were no overt indications of side effects over the duration or of the trial.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims All patents, patent applications and publications referred to herein are hereby incorporated by reference.

We claim:

1. An isolated compound or salt thereof, wherein the compound has the structure:

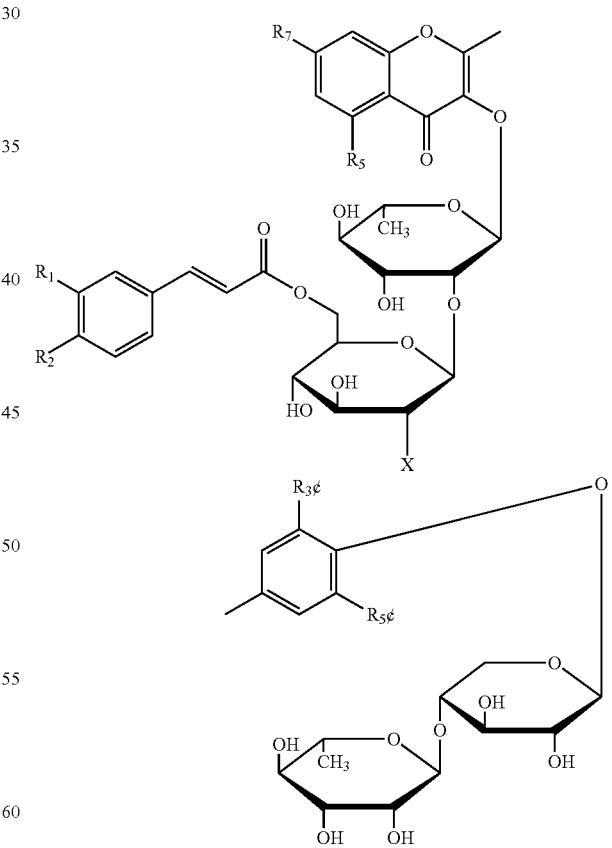

wherein $R^1$, $R^2$, $R^{3'}$, $R^5$, $R^{5'}$, and $R^7$ are independently H, —OH or —OR, wherein R is a $C_1$-$C_6$ alkyl;

X is H, —OH or a glucopyranosyl moiety; and, wherein said compound is not montbretin A or montbretin B.

2. The compound or salt thereof of claim 1, wherein X has the structure:

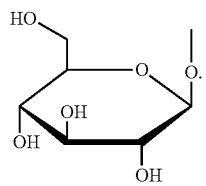

3. The compound or salt thereof of claim 1, wherein $R^{3'}$ and $R^7$ are —OH.

4. The compound or salt thereof of claim 1, wherein each of $R^{3'}$, $R^{5'}$, $R^5$, and $R^7$ are —OH.

5. The compound or salt thereof of claim 1, wherein $R^1$ and $R^2$ are independently H or —OH.

6. The compound or salt thereof of claim 1, wherein $R^2$ is —OH.

7. The compound or salt thereof of claim 1, wherein $R^1$ is —OH.

8. The compound or salt thereof of claim 1, present at an effective amount in a food, beverage, nutritional supplement, pharmaceutical formulation, oral rinse, tooth paste, or chewing gum, wherein the effective amount is for inhibition of salivary or pancreatic α-amylase in a mammalian subject.

9. A composition comprising the compound or salt thereof of claim 1, and one or more physiologically acceptable carriers or excipients.

10. A method of managing postprandial glycemia in a subject in need thereof, wherein said subject is pre-diabetic, has diabetes or is obese, the method comprising administration of an effective amount of a compound or physiologically acceptable salt thereof as defined by claim 1 to manage said postprandial glycemia.

11. A method of treating dental caries and/or plaque in a subject in need thereof, the method comprising administration of an effective amount of a compound or physiologically acceptable salt thereof as defined by claim 1 to treat or prevent dental caries and/or plaque.

12. A method of inhibiting mammalian α-amylase in a mammal in need of α-amylase inhibition, the method comprising administration of an effective amount of a compound or physiologically acceptable salt thereof to inhibit said mammalian α-amylase, wherein the compound has the structure:

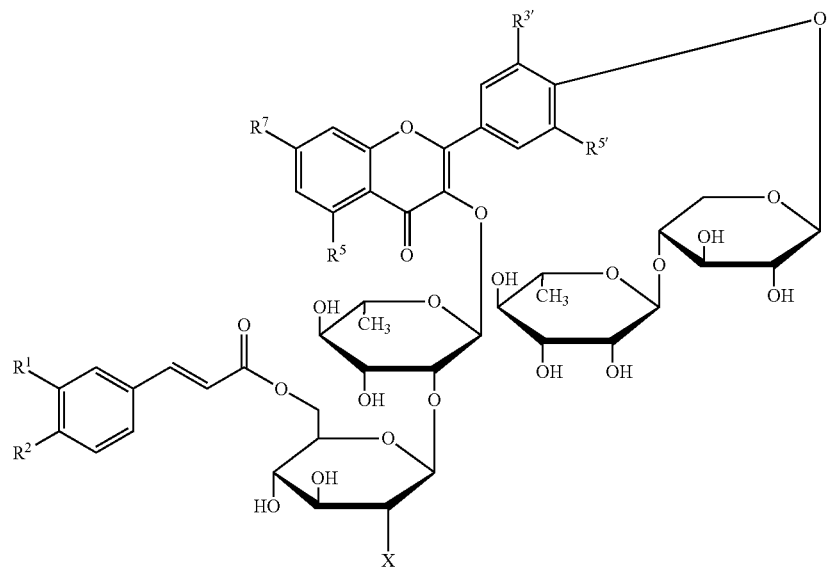

wherein $R^1$, $R^2$, $R^{3'}$, $R^5$, $R^{5'}$, and $R^7$ are independently H, —OH or —OR, wherein R is a $C_1$-$C_6$ alkyl; and
X is H, —OH or a glucopyranosyl moiety.

13. The method of claim 12, wherein $R^{3'}$ and $R^7$ are —OH.

14. The method of claim 12, wherein each of $R^{3'}$, $R^{5'}$, $R^5$ and $R^7$ are —OH.

15. The method of claim 12, wherein $R^1$ and $R^2$ are independently H, —OH and —OMe.

16. The method of claim 12, wherein $R^1$ and $R^2$ are independently H and —OH.

17. The method of claim 12, wherein $R^2$ is —OH.

18. The method of claim 12, wherein $R^1$ is —OH.

19. The method of claim 12, wherein X is:

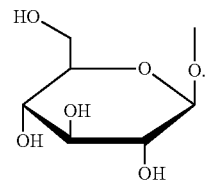

20. The method of claim 12, wherein the compound is montbretin A.

21. The method of claim 12, wherein said compound or salt thereof is present in an extract from corms of *Crocosmia* sp.

22. The method of claim 12, wherein the compound or salt thereof is present in a food, beverage, nutritional supplement, pharmaceutical formulation, oral rinse, tooth paste, or chewing gum.

23. The method of claim 12, wherein the α-amylase is pancreatic α-amylase or salivary α-amylase.

24. The method of claim 12, wherein the mammal is a human.

25. The method of claim 12, wherein the administration is oral administration.

* * * * *

UNITED STATES PATENT AND TRADEMARK OFFICE
CERTIFICATE OF CORRECTION

PATENT NO. : 8,431,541 B2  
APPLICATION NO. : 12/738273  
DATED : April 30, 2013  
INVENTOR(S) : Withers et al.

Page 1 of 2

It is certified that error appears in the above-identified patent and that said Letters Patent is hereby corrected as shown below:

In the Claims

Column 22, claim 1, lines 30-61, delete " 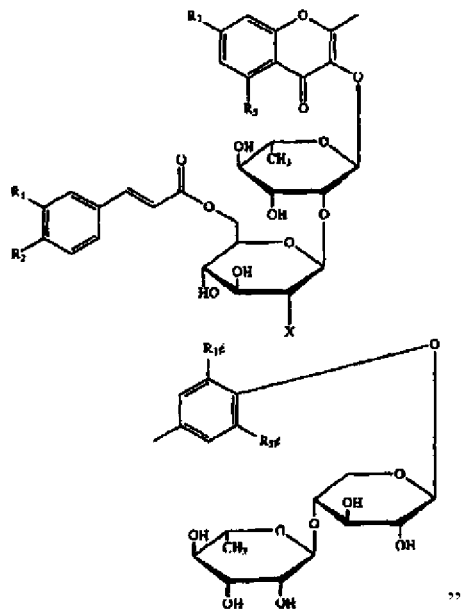 "

Signed and Sealed this  
Eighth Day of April, 2014

Michelle K. Lee  
*Deputy Director of the United States Patent and Trademark Office*

CERTIFICATE OF CORRECTION (continued)
U.S. Pat. No. 8,431,541 B2 and insert -- 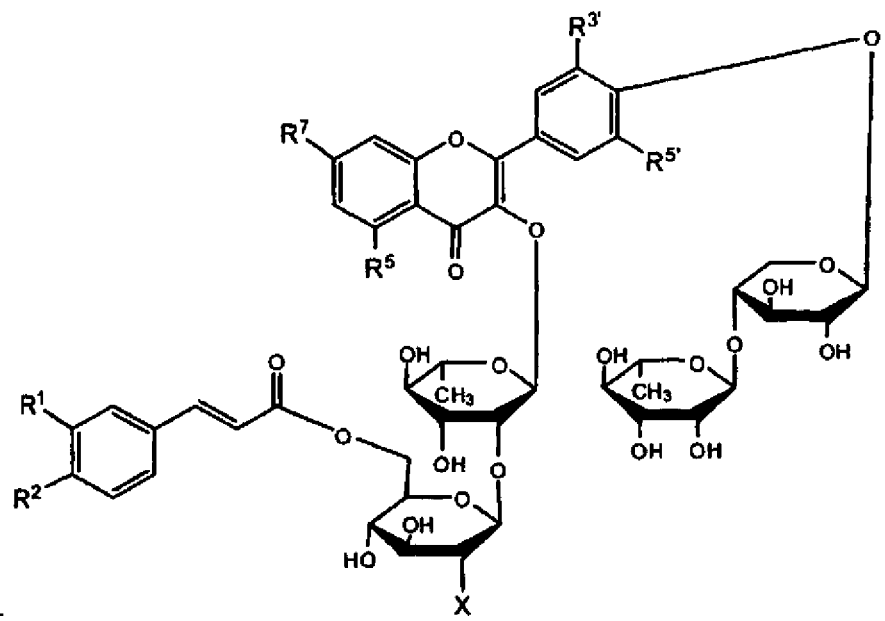 --, therefor.

UNITED STATES PATENT AND TRADEMARK OFFICE
CERTIFICATE OF CORRECTION

PATENT NO. : 8,431,541 B2
APPLICATION NO. : 12/738273
DATED : April 30, 2013
INVENTOR(S) : Withers et al.

It is certified that error appears in the above-identified patent and that said Letters Patent is hereby corrected as shown below:

In the Claims

Column 24, claim 15, line numbers 46-47, delete "wherein $R^1$ and $R^2$ are independently H, -OH and -OMe"

and insert -- wherein $R^1$ and $R^2$ are independently H, -OH or -OMe --, therefor.

Column 24, claim 16, line numbers 48-49, delete "wherein $R^1$ and $R^2$ are independently H and -OH"

and insert -- wherein $R^1$ and $R^2$ are independently H or -OH --, therefor.

Signed and Sealed this
Twenty-first Day of October, 2014

Michelle K. Lee
*Deputy Director of the United States Patent and Trademark Office*